(12) United States Patent
Burton

(10) Patent No.: US 7,384,763 B2
(45) Date of Patent: Jun. 10, 2008

(54) METHOD OF DETECTING β-D-RIBOFURANOSIDASE ACTIVITY

(76) Inventor: Michael Burton, 14 Craven Court, Winwick Quay, Warrington, Cheshire WA2 8QU (GB)

( * ) Notice: Subject to any disclaimer, the term of this patent is extended or adjusted under 35 U.S.C. 154(b) by 272 days.

(21) Appl. No.: 10/493,472

(22) PCT Filed: Oct. 24, 2002

(86) PCT No.: PCT/GB02/04815

§ 371 (c)(1),
(2), (4) Date: Apr. 23, 2004

(87) PCT Pub. No.: WO03/035897

PCT Pub. Date: May 1, 2003

(65) Prior Publication Data

US 2004/0259181 A1   Dec. 23, 2004

(30) Foreign Application Priority Data

Oct. 24, 2001   (GB)   .................................. 0125528.0
Sep. 18, 2002   (GB)   .................................. 0221716.4

(51) Int. Cl.
*C12Q 1/04* (2006.01)
(52) U.S. Cl. .......................................... 435/34; 435/18
(58) Field of Classification Search .................. 435/18, 435/34
See application file for complete search history.

(56) References Cited

U.S. PATENT DOCUMENTS 6,764,829 B2 * 7/2004 Schramm et al. ............. 435/18
2004/0235081 A1 * 11/2004 Burton ......................... 435/23
2005/0124556 A1 * 6/2005 Burton ......................... 514/23

FOREIGN PATENT DOCUMENTS

FR     2 770 538         11/1997
WO     WO 97/31008       8/1997

OTHER PUBLICATIONS

Kang, E. et al. A Novel And Simple Colorimetric Method for Screening Giardia intestinalis and Anti-Giardial Activity in vitro. Parasitology 1998 vol. 117, pp. 229-234.*
Masao Shiozaki, "Synthesis of 4',8-dihydroxyisoflavon-7-yl D-arabinofuranoside" Exploratory Chemistry Research Laboratories pp. 1477-1742 dated 1999.
Berlin et al. XP-002271582 "In Situ Color Detection of L-Arabinofuranosidase, a" No-Background Reporter Gene, with 5-Bromo-3-indolyl-a -L-arabinofuranoside pp. 171-174 (dated 1996).
XP-002214084 (abstract only), Dec. 1998.
XP-002214085 (abstract only), Jan. 1997.
M. Barber et al.; "Identification of Staphylococcus Pyogenes by the Phosphatase Reaction"; J. Path. Bact.—vol. LXIII; pp. 65-68, no date given.
G. Dahlen et al.; "Screening Plate Method for Detection of Bacterial B-Glucuronidase"; Applied Microbiology, Dec. 1973, pp. 863-866.
M. Kilian et al.; "Rapid Identification of Enterobacteriaceae"; Acta path. microbiol. scand. Sect. B, 87, 1979, pp. 271-276.

* cited by examiner

*Primary Examiner*—Ralph Gitomer
(74) *Attorney, Agent, or Firm*—Whitham Curtis Christofferson & Cook, PC

(57) ABSTRACT

This invention provides new methods for detecting enzyme activity using enzyme substrates comprising an enzyme cleavable portion and a chromogenic portion. The enzyme cleavable portion is a β-D-ribofuranosyl group and the chromogenic portion forms a detectable indicator following enzyme cleavage. In one aspect of this invention the chromogenic β-D-riboforanoside substrate forms a colored substantially non-diffusable indicator. A second aspect of this invention provides novel chromogenic β-D-ribofuranosides.

27 Claims, No Drawings

METHOD OF DETECTING β-D-RIBOFURANOSIDASE ACTIVITY

This invention relates to chromogenic enzyme substrates.

Indicator enzyme substrates comprise an enzyme cleavable portion (eg a monosaccharyl) and a portion which forms a detectable indicator on cleavage (eg a chromogenic or fluorogenic group). A large number of glycoside-based enzyme substrates are known and are used extensively in microbiology, molecular biology and other fields. Glycosides of many different carbohydrates have been synthesised and utilised for detection purposes. The enzymes that are detected by these glycosides are often group specific (i.e. show relatively little specificity towards one portion of the substrate upon which they act) and therefore a wide variety of aglycones (i.e. indicator portions) can be tolerated. Thus, in the case of β-galactosidase many different β-galactosides have been used in the detection of it. Examples include o-nitrophenyl-, p-nitrophenyl-, indoxyls-(5-bromo-4-chloro-3-indolyl and 6-chloro-3-indolyl), 4-methylumbelliferyl-, 2-naphthyl-, 6-bromo-2-naphthyl-, cyclohexenoesculetin-(CHE), alizarin-, naphthol-ASBI- and phenyl-β-galactosides. Glycosides containing glucuronic acid, glucose, galactose, mannose, fucose, arabinose, N-acetylglucosamine, N-acetylgalactosamine, sialic acid, xylose, and cellobiose carbohydrate moieties are amongst those most frequently encountered in enzyme substrate applications. Many of these, such as β-D-glucuronides, α- and β-D-galactopyranosides and α- and β-D-glucopyranosides have found widespread use in the identification and enumeration of bacteria in areas such as clinical, food, veterinary, environmental and water microbiology. At the present time there are numerous commercial media and test kits available containing enzyme substrates, which show the presence of bacteria by the generation of coloured colonies or solutions.

Some compounds containing a sugar moiety which is ribose are known. For example ribofuranosides of DOPA (2-amino-3-(3,4-dihydroxyphenyl)propanoic acid) and DOPA derivatives, are desired by Chavis et al (1981). Eur. J. Med. Chem.-Chim. Ther. 16(3), 219-227. The compounds have potential use as anti-hypertensives.

This invention provides novel methods of using β-D-ribofuranosides and novel β-D-ribofuranoside indicator enzyme substrates. Until the present time, substrates based on β-D-ribofuranoside have had little application as substrates. This invention also provides some novel β-D-ribofuranoside compounds.

Some potential or actual substrates based on β-D-ribofuranoside (BDRF) are known. p-Nitrophenyl-BDRF was first reported in 1976 (K. Honma et al, *Chem. Pharm. Bull.*, 1976, 24, 394-399) but its use as an enzyme substrate was not reported at that time.

4-Methylumbelliferyl-β-D-ribofuranoside (4-MU-BDRF) has been commercially available from Glycosynth (Warrington, UK) since 1995. The indicator formed from 4-MU is detectable fluorimetrically, and not using visible incident light or being detectable by eye.

In WO97/31008 Schramm et al describe the synthesis and use of some BDRF and BDRF phosphate substrates for the detection of parasites in biological samples. This method involves the detection of nucleoside hydrolase or nucleoside phosphorylase activity in the sample. The substrates are chromogenic or fluorogenic. One example is 4-MU-BDRF. Schramm et al also discloses p-nitrophenyl β-D-ribofuranoside. This substrate was not tested against bacteria, yeast or their enzymes. p-Nitrophenyl β-D-ribofuranoside-5-phosphate was tested against an N-ribohydrolase from *E. coli*, namely AMP nucleosidase, and was found to be inactive.

In addition, none of the BDRF substrates previously described are ideally suited for use in plated (solid) media because they diffuse extensively or, in the case of 1-naphthyl-BDRF, would require a post incubation coupling technique to form a coloured precipitate. In order to establish the utility of β-D-ribofuranoside for the identification of microbes on solid media (e.g. agar) we therefore required a substrate that would show highly localised enzyme activity.

This invention provides a method of detecting β-D-ribofuranosidase activity on a solid medium including a) contacting on a solid medium a chromogenic β-D-ribofuranoside, comprising a β-D-ribofuranosyl group and a chromogenic portion, said chromogenic portion being cleavable by β-D-ribofuranosidase from the β-D-ribofuranosyl group releasing the chromogenic product and forming an indicator which is or is formed from the chromogenic product and is substantially non-diffusible in the solid medium, with a substance suspected of containing β-D-ribofuranosidase activity b) detecting whether β-D-ribofuranosidase activity is present by determining whether said indicator is formed.

β-D-Ribofuranosidase activity is an enzyme activity capable of cleaving β-D-ribofuranosyl groups.

It is an advantage of this invention that the substantially non-diffusable indicator forms directly after the chromogenic β-D-ribofuranoside is contacted with the substance suspected of containing β-D-ribofuranosidase activity, that is a post incubation step is not required. The cleaved chromogenic portion called the chromogenic product may form the indicator. Alternatively, however, the chromogenic product may need to be contacted with a developer, another substance needed to facilitate formation of the coloured substantially non-diffusable indicator. Therefore the above described method may also involve contacting the chromogenic product with a developer required for formation of the said indicator. The action of the developer is preferably rapid and concurrent with the process of method step a) and does not require a change in conditions.

It is envisaged that the method of this invention will be useful for substances suspected of containing β-D-ribofuranosidase activity obtained from a wide variety of sources. It is especially envisaged that the above described method will be carried out wherein the substance suspected of containing β-D-ribofuranosidase activity comprises a substance of microbial origin, preferably of bacterial origin. In such a procedure the above described method may include a preliminary step of growing microbes on the solid medium.

It is generally expected that the chromogenic β-D-ribofuranoside is present in the solid medium in a preliminary step of growing the microbes on the solid medium and in step a). In an embodiment which requires a developer to contact the cleaved chromogenic portion for formation of a coloured substantially non-diffusable indicator it is generally expected that it is present in the solid medium too. It is possible that the chromogenic β-D-ribofuranoside and any required developer are added to the surface of the solid medium in the method of this invention, but preferably they are distributed through the solid medium.

The substantially non-diffusible indicators produced by the method of this invention is coloured. As a result the indicator is visible by eye, preferably using visible incident light. As the skilled person will understand, this is an advantage because detection step b) may be carried out rapidly and easily.

Another aspect of this invention provides a method of detecting β-D-ribofuranosidase activity including a) contacting a chromogenic β-D-ribofuranoside comprising a β-D-ribofuranosyl group and a chromogenic or fluorogenic portion with a sample comprising a substance of bacterial origin suspected of containing β-D-ribofuranosidase activity b) detecting whether β-D-ribofuranosidase activity is present by detecting the presence of an indicator formed from the cleaved chromogenic product.

In this method the chromogenic portion may comprise any group which provides a detectable (in the visible spectrum) difference between the cleaved and uncleaved moiety. It is preferred that this method is carried out on a solid medium and the chromogenic indicator is substantially non-diffusible. It is preferred that the product be detected by the eye, but other spectroscopic means which detect visible light may be used.

For both aspects of this invention, when the β-D-ribofuranosidase activity is of bacterial origin it is preferred that the bacteria are selected from the genus *Yersinia,* the genus *Shigella,* the genus *Vibrio,* and *Corynebacterium diphtheriae* and *Arcanobacterium haemolyticum.* It is important that these bacteria can be successfully detected since *Yersinia enterocolitica* can cause diarrhoea and at present there are no commercial media which contain enzyme substrates that can detect it and differentiate it from similar species. *Shigella* species can cause dysentery, *Vibrio* species are significant in food poisoning and can cause cholera and *Corynebacterium diphtheria* causes diphtheria.

Following enzyme activity the cleaved chromogenic portion directly forms a coloured, e.g. non-diffusible, indicator. The chromogenic portion of these compounds is selected from a 1,2-dihydroxybenzene, preferably a catechol residue, a cyclohexenoesculetin moiety or another esculetin moiety or an alizarin moiety, an indoxyl moiety or a p-naphtholbenzein moiety and their derivatives. A catechol residue for the present specification is a moiety resulting from removal of one or both hydroxylic hydrogen atoms from a 1,2-dihydroxybenzene or a substituted derivative thereof, preferably substituted with a derivatising moiety which is linked to the aromatic ring of the catechol via a bond but excluding compounds with rings fused to the 1,2-dihydroxy benzene ring, such as in an esculetin or alizarin compound. When the chromogenic portion is formed from catechol or a catechol derivative in which a derivatising moiety is linked to the catechol ring via a bond the chromogenic portion may for example be formed from a dihydroxybenzaldehyde, dihydroxybenzophenone, dihydroxyflavonoid, dihydroxyaurone or dihydroxychalcone structure.

The ribofuranosides are produced by a condensation reaction between the ribofuranose in appropriately protected form and the precursor of the chromogenic portion which has a free hydroxyl group, to generate a glycoside linkage. Generally on condensation of the β-D-ribofuranose and the chromogenic portion the oxygen atom which is retained in the linkage was originally part of the starting material giving rise to the chromogenic portion.

When the chromogenic portion of the chromogenic β-D-ribofuranoside is formed from a 1,2-dihydroxy benzene, especially a catechol or catechol derivative, a metal ion may be used as the developer. The metal ion is chelated by the cleaved chromogenic portion to produce a coloured substantially non-diffusable indicator. Especially preferred chelatable metal ion compounds are iron salts, aluminium salts and bismuth salts.

The chromogenic enzyme substrate can be represented by the following formulae

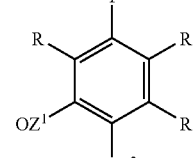

I

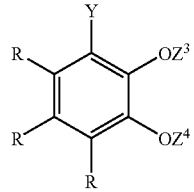

II where Y and R are moieties which do not interfere with enzyme cleavage or formation of the indicator and each of $Z^1$, $Z^2$, $Z^3$ and $Z^4$ can be H or a β-D-ribofuranosyl group, provided $Z^1$ and $Z^2$ or $Z^3$ and $Z^4$ are not simultaneously H.

A β-D-ribofuranosyl group Z has the following structure:

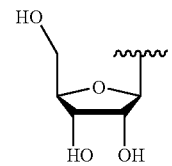

where

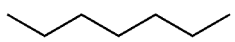

indicates the linkage to the phenolic oxygen above in the general formula I or II.

In one embodiment Y and R are organic moieties containing less than 40 atoms, preferably less than 30 atoms and more preferably less than 20 atoms.

In the above structures Y can be an organic moiety. Preferably Y comprises a substituted or unsubstituted aryl or heteroaryl group containing 5 to 18 ring atoms. In a preferred embodiment Y is an organic moiety with a core structure of V or VI

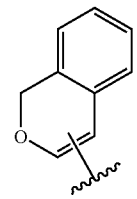

V

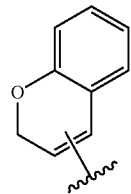

VI wherein the structures are linked to the catechol ring as shown.

Core structure in this specification means the skeleton of Y, and this may further be substituted.

It is preferred that Y has the structure of VII or VIII

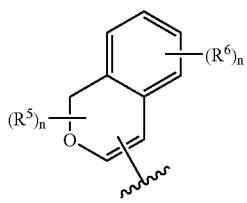

VII

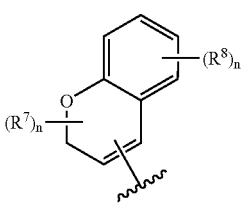

VIII wherein each of $(R^5)_n$, $(R^6)_n$, $(R^7)_n$ and $(R^8)_n$ may represent more than one non-hydrogen substituent and include =O. $R^5$, $R^6$, $R^7$ and $R^8$ are substituents which do not interfere with enzyme action or metal ion chelation. n is preferably 0, 1 or 2.

The most preferred embodiments of Y are represented by structures IX and X

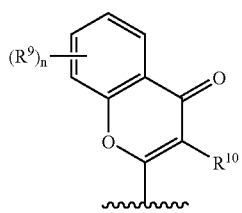

IX

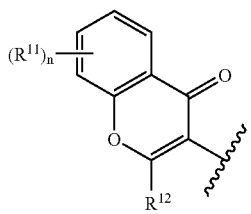

X wherein $(R^9)_n$, and $(R^{11})_n$ represent one or more substituents and $R^{10}$ and $R^{12}$ are each hydrogen or a substituent, all of which do not interfere with enzyme action or metal ion chelation.

In embodiments where $(R^6)_n$, $(R^8)_n$, $(R^9)_n$ and $(R^{11})_n$ represent more than one substituent including =O the bonds of the ring are rearranged. $R^9$ and $R^{11}$ are preferably selected from the group consisting of hydroxyl, $C_{1-24}$-alkyl, $C_{2-24}$-alkenyl, $C_{1-6}$-alkoxy, acyl including —CHO and COPhe where Phe is phenyl, =O, halogen, nitro, aryl and acyloxy groups. Alkyl and aryl groups may be substituted with amino, hydroxyl, peptide, acyloxy, alkoxy, —CONH$_2$, CONHR$^1$ and NHCOR$^1$, in which R$^1$ is an alkyl or aryl group, and aryl groups. $R^{10}$ and $R^{12}$ are selected from the same groups as $R^9$ and $R^{11}$ and additionally hydrogen. Preferably $R^9$, $R^{10}$, $R^{11}$ and $R^{12}$ are selected from $C_{1-4}$-alkoxy.

In the above structures R can be H, $C_1$ to $C_6$-alkyl, -alkoxy and -hydroxyalkyl, halogeno, nitro, acyl, aryl and amido groups, or two adjacent groups R may be joined to form a fused ring system with the ring shown in formulae I and II, such a fused ring generally having an aromatic character, and optionally including one or more heteroatoms. Preferably each group R is monofunctional, i.e. is not joined to any other group R, that is the compound is a catechol.

The chromogenic β-D-ribofuranoside is preferably selected from catechol-β-D-ribofuranoside, 3',4'-dihydroxyflavone-4'-β-D-ribofuranoside, quercetin-4'-β-D-ribofuranoside, 3,4-dihydroxybenzaldehyde-4-β-D-ribofuranoside, 3,4-dihydroxychalcone-4-β-D-ribofuranoside, 4-nitrocatechol-1-β-D-ribofuranoside, 3,3',4'-trihydroxyflavone-4'-β-D-ribofuranoside, 3',4'-dihydroxy-3-methoxyflavone-4'-β-D-ribofuranoside, 3',4'-dihydroxyaurone-4'-β-D-ribofuranoside and 3-indolyl-β-D-ribofuranosides having one or more halogen or nitro substituents and/or N-lower alkyl substituents.

A further aspect of this invention provides novel chromogenic β-D-ribofuranoside enzyme substrates in which the chromogenic moiety is a 1,2-dihydroxy benzene residue. In the substrate one or both of the hydroxylic oxygen atoms of the residue is used to link to a β-D-ribofuranosyl group. These novel compounds may be represented by formulae I and II above provided that Y is not a substituted alkyl group when all R groups are H. In a preferred class of novel substrates the compounds are catechols, in which no two R groups are fused.

Novel indoxyl ribofuranoside compounds are claimed in our copending application filed on the same day as the present application under reference HMJ03602WO.

Preferred novel chromogenic-β-D-ribofuranosides have the structural formula I or II as described above wherein Y may have the structural formulae of V, VI, VII, VIII, IX or X.

Preferred novel chromogenic β-D-ribofuranosides have a catechol residue formed from a catechol, nitrocatechol, dihydroxyflavonoid such as dihydroxyflavone, dihydroxyisoflavone, dihydroxyflavanone, dihydroxyisoflavanone, dihydroxyflavan, trihydroxyflavan or dihydroxyisoflavan, dihydroxyaurone, dihydroxychalcone, dihydroxybenzaldehyde, dihydroxybenzophenone, or dihydroxybenzaldehydesemicarbazone, or quercetin and their derivatives. Quercetin is also called 3,5,7,3',4'-pentahydroxyflavone.

Especially preferred novel compounds include catechol-β-D-ribofuranoside, 3',4'-dihydroxyflavone-4'-β-D-ribofuranoside, quercetin-4'-β-D-ribofuranoside, 3,4-dihydroxybenzaldehyde-4-β-D-ribofuranoside, 3,4-dihydroxychalcone-4-β-D-ribofuranoside, 4-nitrocatechol-1-β-D-ribofuranoside, 3,3',4'-trihydroxyflavone-4'-β-D-ribofuranoside, 3',4'-dihydroxy-3-$C_{1-6}$-alkoxyflavone-4'-β-D-ribofuranoside and 3',4'-dihydroxyaurone-4'-β-D-ribofuranoside, 3,4-dihydroxybenzaldehydesemicarbazone-4-β-D-ribofuranoside and their derivatives.

A general scheme for the synthesis of a substrate comprising a catechol residue involves β-D-ribofuranose with protected hydroxyl groups being mixed together with catechol or a catechol derivative and a catalyst to form the catechol (derivative) β-D-ribofuranoside. Optionally further derivatising moieties may be added to the catechol residue. The product is deprotected and the chromogenic enzyme substrate is purified. Indoxyl ribofuranosides may be made by an analogous process. A specific example is in. Example 4 below.

The β-D-ribofuranosides based on 1,2-dihydroxy benzene residues may be produced as the hydrate or in the form of a suitable salt. The salts could be derived from either metal or organic ions.

The components required for carrying out the methods of this invention may be presented as a kit of components. Such a kit would include a chromogenic β-D-ribofuranoside comprising a β-D-ribofuranosyl group and a chromogenic portion which when cleaved directly forms a coloured substantially non-diffusible indicator. Alternatively such a kit would include a chromogenic β-D-ribofuranoside which when cleaved by bacteria or a substance of bacterial origin produces a detectable indicator.

Such a kit of components may also comprise a developer. The skilled person will appreciate that it would be useful to produce a solid medium which can support the growth of microbes and comprises the kit components mentioned above. Therefore the above described kits may also include components necessary to produce said solid medium. The kit components may be packaged separately or in various combinations depending on the requirements of the analysis procedure to be carried out.

It may be useful for the media used in detecting β-D-ribofuranosidase activity to contain other components which detect other enzyme activity or select for specific microbes. Therefore kits of this invention may also include such compounds.

The limitations of using a substrate which generates a diffusible end product after hydrolysis on a solid medium are known by those skilled in the art. The inventor has demonstrated the utility of the non-diffusible indicators of this invention. For example a culture plate was prepared containing solid medium and the chromogenic enzyme substrate 3',4'-dihydroxyflavone-4'-β-D-ribofuranoside along with ferric ion. A culture containing roughly equal numbers of *Escherichia coli* (β-D-ribofuranosidase positive) and *Acinetobacter lwoffii* (β-D-ribofuranosidase negative) was grown on the medium. *E. coli* produced intense black colonies due to hydrolysis of 3',4'-dihydroxyflavone-4'-β-D-ribofuranoside and there was little or no diffusion of the coloured indicator away from those colonies. The *A. lwoffii* colonies were colourless. It was possible to differentiate the two species even when the colonies were virtually coincident.

EXAMPLE 1

This example provides synthetic methods for several chromogenic β-D-ribofuranosides.

EXAMPLE 1.1

Synthesis of 3',4'-Dihydroxyflavone-4'-β-D-ribofuranoside sodium salt (DHF-riboside)

A 50 ml round bottomed flask equipped with a stopper and a magnetic stirrer was charged with 3',4'-dihydroxyflavone (DHF) (Lancaster Synthesis Ltd, Lancashire, UK) (500 mg), β-D-ribofuranose tetraacetate (640 mg), 3 Å molecular sieves (5.2 g) and dichloromethane (20 ml). The mixture was stirred for 15 min., then the boron trifluoride diethyl etherate catalyst (2.0 ml) was added in one portion. Stirring was continued for a further 20 min, then the reaction mixture was poured into a solution of saturated sodium bicarbonate (150 ml). The organic layer was diluted by the addition of more dichloromethane (30 ml) and then separated from the yellow aqueous layer in a separating funnel. The organic layer was then washed eleven times with an equal volume of saturated sodium bicarbonate solution then dried for one hour over magnesium sulfate. After removal of the drying agent, evaporation of the dichloromethane yielded the glycoside triacetate as a dark gum (390 mg). To this gum (315 mg) was added a sodium methoxide solution that had been made by dissolving sodium (50 mg) in methanol (5 ml). After agitating for a few minutes the gum dissolved and the solution was left at ambient temperature for 16 hours. The solution was then concentrated to a volume of approximately 2 ml by evaporation after which addition of diethyl ether (10 ml) caused the product to precipitate. It was collected by vacuum filtration and, after washing with diethyl ether (20 ml) in four portions was immediately transferred to a desiccator and dried over phosphorous pentoxide under vacuum for 2 hours. The product so obtained was a yellow powder (201 mg).

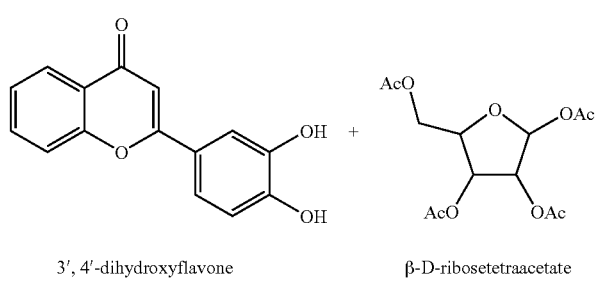

3', 4'-dihydroxyflavone     β-D-ribosetetraacetate

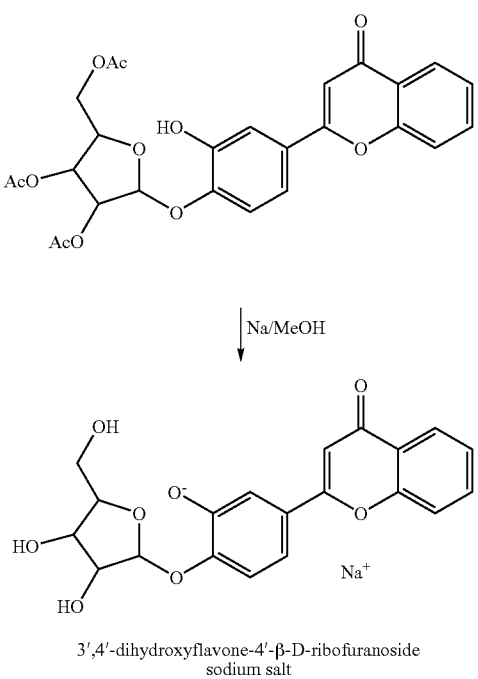

3',4'-dihydroxyflavone-4'-β-D-ribofuranoside
sodium salt

EXAMPLE 1.2

Synthesis of Catechol-β-D-ribofuranoside sodium salt (2-Hydroxyphenyl-β-D-ribofuranoside sodium salt)

A 500 ml round bottomed flask equipped with a magnetic stirrer was charged with catechol (33 g), 3 Å molecular sieves (20 g), and dichloromethane (200 ml). The solution which formed was stirred for 10 minutes, then boron trifluoride diethyl etherate (10 ml) was added in one portion. After 1 hour the reaction mixture was filtered, then it was washed in a separating funnel sequentially with equal volumes of saturated sodium bicarbonate (five times) and de-ionised water (twice), then dried over magnesium sulfate. Removal of the drying agent and evaporation afforded a pale yellow oil that slowly solidified. The solid was dissolved in hot industrial methylated spirits (IMS) (50 ml) and then stored at 4° C. for 16 hours to allow crystallisation to complete. The white solid was collected by vacuum filtration and washed with IMS (20 ml) in two portions. After one day drying in air the yield of protected riboside was 17.1 g. The protected riboside (15 g) was suspended in methanol (150 ml) and a solution made up of sodium (2 g) in methanol (50 ml) was added to it. Initially the solid dissolved but this was soon replaced by a heavy precipitate. The reaction mixture was set aside for 16 hours. The solid was then collected by vacuum filtration and washed with methanol (5 ml). The hygroscopic solid was then immediately transferred to a desiccator and dried under vacuum over phosphorous pentoxide for 6 hours. The yield of white powder was 4.3 g.

added in one lot and stirring was then continued for a further 20 minutes whereupon the molecular sieves were removed by filtration. The filtrate was washed with an equal volume of saturated sodium bicarbonate four times, dried over magnesium sulfate for 1 hour then evaporated to dryness. The residual pale yellow solid was dissolved in hot IMS (70 ml), and stored at 4° C. for 6 hours. The product was harvested by filtration. Drying over phosphorous pentoxide under vacuum afforded 12.4 g of an off-white solid.

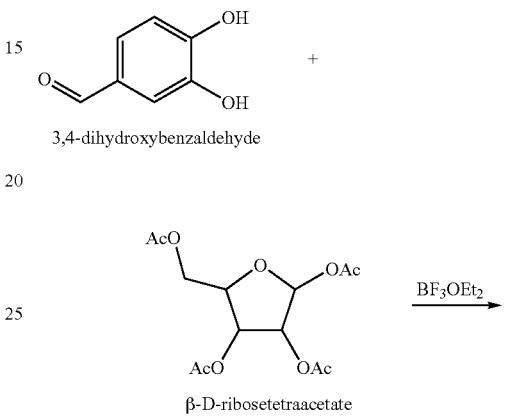

3,4-dihydroxybenzaldehyde

β-D-ribosetetraacetate

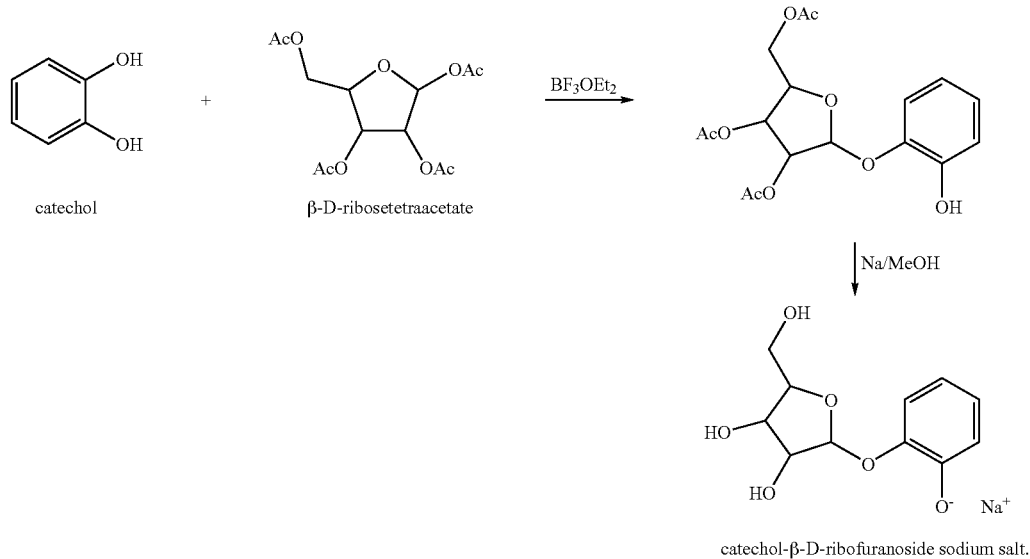

catechol

β-D-ribosetetraacetate catechol-β-D-ribofuranoside sodium salt.

EXAMPLE 1.3

Synthesis of 3,4-Dihydroxybenzaldehyde-4-β-D-ribofuranoside triacetate

To a 3 L round bottomed flask provided with a magnetic stirrer was added 3,4-dihydroxybenzaldehyde (50 g), β-D-ribofuranose tetraacetate (47 g), 3 Å molecular sieves (350 g) and dichloromethane (1.4 L). After stirring this mixture for 5 minutes boron trifluoride diethyl etherate (75 ml) was -continued

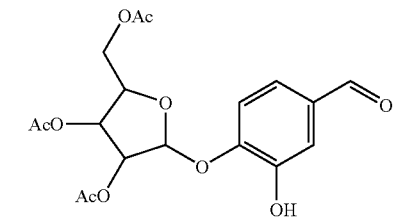

3,4-dihydroxybenzaldehyde-β-D-ribofuranoside triacetate

EXAMPLE 1.4

Synthesis of 3,4-Dihydroxybenzaldehyde-4-β-D-ribofuranoside sodium salt

To a mixture of 3,4-dihydroxybenzaldehyde-4-β-D-ribofuranoside triacetate (from Example 1.3) (5.0 g) in methanol (25 ml) was added a solution of sodium (0.5 g) in methanol (20 ml). The triacetate dissolved and was replaced by a dense precipitate. After 5 hours this was filtered off under vacuum and washed on the filter with methanol (5 ml) and diethyl ether (10 ml). Drying for 4 hours under vacuum over phosphorous pentoxide gave the product as a pale cream solid (3.1 g).

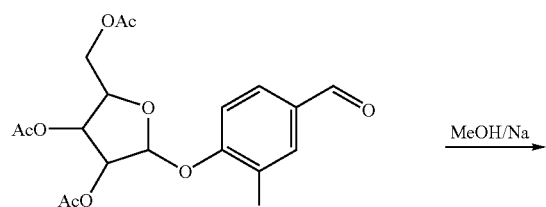

3,4-dihydroxybenzaldehyde-β-D-ribofuranoside triacetate

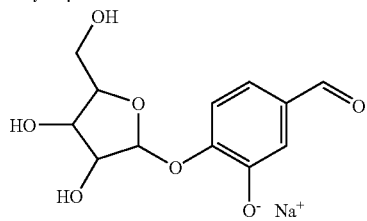

3,4-dihydroxybenzaldehyde-β-D-ribofuranoside sodium salt

EXAMPLE 1.5

Synthesis of 3,4-Dihydroxybenzaldehydesemicarbazone-4-β-D-ribofuranoside

To a solution of 3,4-dihydroxybenzaldehyde-4-β-D-ribofuranoside sodium salt (from Example 1.4) (0.5 g) in de-ionised water (5 ml) was added a solution of semicarbazide hydrochloride (1 g) and potassium acetate (1.5 g) in water (5 ml). The mixture was heated in a boiling water bath for 10 minutes then allowed to cool. After concentrating the solution to half its original volume by evaporation the product crystallised out. It was collected by vacuum filtration and, after washing with water (2 ml), it was dried in a desiccator in vacuo over phosphorous pentoxide. The product was a white solid (300 mg).

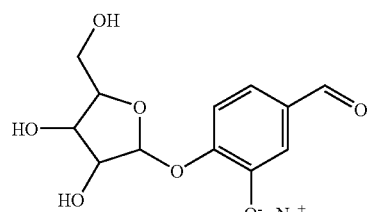

3,4-dihydroxybenzaldehyde-β-D-ribofuranoside sodium salt

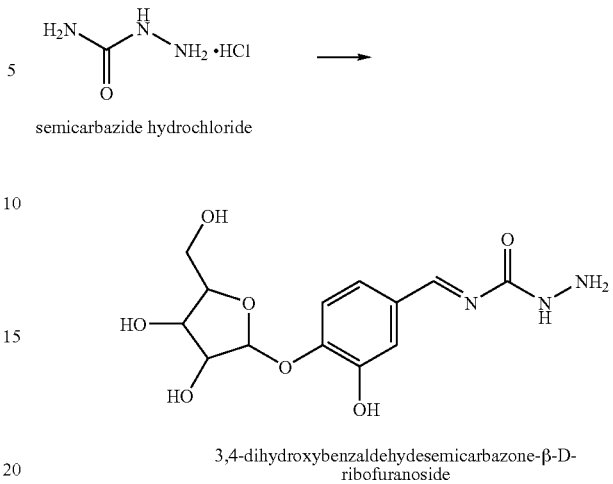

semicarbazide hydrochloride 3,4-dihydroxybenzaldehydesemicarbazone-β-D-ribofuranoside

EXAMPLE 1.6

Synthesis of 3,4-Dihydroxychalcone-4-β-D-ribofuranoside

To a solution of 3,4-dihydroxybenzaldehyde-4-β-D-ribofuranoside sodium salt (from Example 1.4) (0.25 g) in IMS was added sodium hydroxide (0.1 g) in de-ionised water (3 ml) and acetophenone (0.1 g). The mixture was stirred at room temperature for 9 days after which time the reaction was evaporated to dryness. The product was obtained as a red solid.

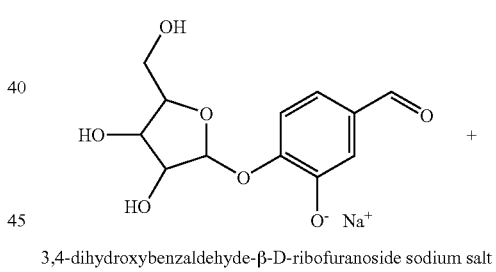

3,4-dihydroxybenzaldehyde-β-D-ribofuranoside sodium salt

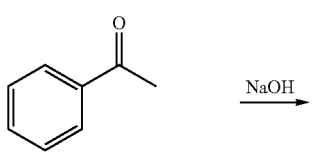

acetophenone

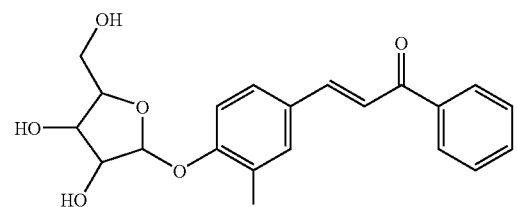

3,4-dihydroxychalcone-β-D-ribofuranoside

EXAMPLE 1.7

Synthesis of 3',4'-Dihydroxyaurone-4'-β-D-ribofuranoside

To a mixture of 3,4-dihydroxybenzaldehyde-4-β-D-ribofuranoside triacetate (from Example 1.3) (0.4 g) and 3-coumaranone (0.17 g) in IMS (20 ml) was added a solution of IMS saturated with hydrogen chloride gas (0.05 ml). The mixture was stirred at room temperature for 3 days and then evaporated to dryness. The resulting solid was dissolved in methanol (2 ml) and a solution of sodium (50 mg) in methanol (0.5 ml) was added giving a blood-red solution. This solution was evaporated to dryness and partitioned between de-ionised water (25 ml) and dichloromethane (50 ml). The aqueous layer was extracted with two further dichloromethane washes (50 ml) before being evaporated to dryness. The product was obtained as a red solid.

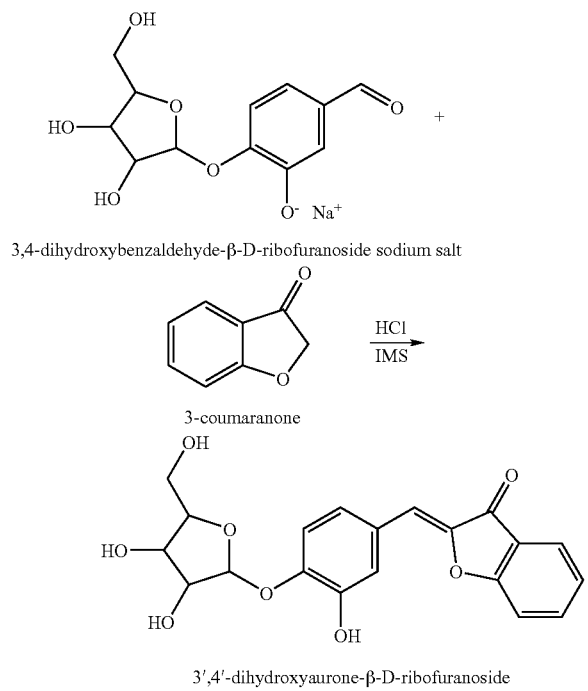

EXAMPLE 2

This example provides an evaluation of the ribofuranoside of 3',4'-dihydroxyflavone (produced in Example 1.1) (DHF-riboside).

The ribofuranoside derivative of dihydroxyflavone was tested with 194 distinct strains of bacteria. The choice of bacteria included a wide range many of which are important pathogens or commensals commonly isolated from pathological samples.

The chromogenic β-D-ribofuranoside substrate was added to Columbia agar at a substrate concentration of 300 mg/l. Ferric ammonium citrate was included at 500 mg/l. All ingredients were autoclaved at 116° C. for 20 minutes to ensure sterilisation. Agar plates were then prepared in 90 mm petri dishes. The substrate caused a yellow colouration of the agar.

For each strain tested, a bacterial suspension was prepared in sterile deionised water at an inoculum of approximately $1.5 \times 10^8$ colony forming units per ml. This was achieved using a densitometer. 1 μl of each bacterial suspension was then inoculated onto each plate using a multipoint inoculator. Strains were inoculated in parallel onto Columbia agar containing ferric ammonium citrate with no substrate (negative control).

After 18 hours incubation, strains were examined visually for the presence of colour. Any strains producing a black colouration on substrate containing media but not on the negative control plates were deemed to be hydrolysing the substrate.

Of 120 Gram negative bacteria tested 68.3% hydrolysed DHF-riboside. Those which were positive produced a clearly visible black chelate of 3',4'-dihydroxyflavone and ferric ammonium citrate which remained restricted to bacterial colonies without diffusion into the surrounding agar. Detection of β-D-ribofuranosidase activity allowed for distinctions to be made between closely related genera or species. Most of the *Enterobacteriaceae* tested were strongly positive for β-D-ribofuranosidase activity. An exception was *Yersinia enterocolitica*, a pathogen which is a cause of enteritis. This substrate could have a useful role for differentiation of this species from closely related bacteria. The fact that *Shigella* genus was uniformly positive for β-D-ribofuranosidase activity was also notable. None of the glycosidases commonly sought in diagnostic microbiology are uniformly produced by species of *Shigella* and this is a limiting factor in designing methods for their detection. This invention may allow for distinction between *Shigella* and closely related species such as *Proteus*.

A further point of interest among the activities of Gram-negative bacteria concerns the *Vibrionaceae*. Currently available culture media for the detection of *Vibrio* species do not allow for the differentiation of *Aeromonas* species which is commonly found in the environment and is very closely related to *Vibrio*. Most of the *Vibrio* species tested here, including the two main pathogens *V. cholerae* and *V. parahaemolyticus*, do not express β-D-ribofuranosidase. This is in contrast to *Aeromonas* species which are highly active. This invention may allow for a simple means of differentiating between these two closely related species.

Among the Gram-positive bacteria tested only 30.8% were active with this substrate. All of the staphylococci were positive but there was no differentiation between the different species of staphylococci tested. Streptococci were almost universally negative whereas enterococci ('faecal streptococci') were variable in their activity. The main point of interest was that *Corynebacterium diphtheriae* and *Arcanobacterium haemolyticum* were active with this substrate. Both of these species are found in the throat of infected humans and throat cultures are therefore performed to isolate and identify these pathogens. The aerobic commensal flora of the throat is dominated by streptococci and DHF-riboside of this invention may provide a means of differentiating these two pathogens from the normal commensal flora of the throat.

TABLE 1

Hydrolysis of 3'4'-dihydroxyflavone-β-ribofuranoside by gram negative bacteria

| Strain | Reference No. | β-Riboside |
|---|---|---|
| *E. coli* 0157 | NCTC 12079 | ++ |
| *E. coli* 0157 | NCTC 12080 | ++ |
| *E. coli* 0157 | NCTC 12900 | ++ |
| *E. coli* 0157 | NCTC 13125 | ++ |
| *E. coli* 0157 | NCTC 13126 | ++ |
| *E. coli* 0157 | NCTC 13127 | ++ |
| *E. coli* 0157 | NCTC 13128 | ++ |
| *E. coli* | NCTC 10418 | ++ |
| *E. coli* | ECO 2 | ++ |
| *E. coli* | ECO 3 | ++ |
| *E. coli* | ECO 4 | ++ |

TABLE 1-continued

Hydrolysis of 3'4'-dihydroxyflavone-β-ribofuranoside by gram negative bacteria

| Strain | Reference No. | β-Riboside |
|---|---|---|
| E. coli | ECO 5 | ++ |
| E. coli | ECO 6 | ++ |
| E. coli | ECO 7 | ++ |
| E. coli | ECO 8 | ++ |
| E. coli | ECO 9 | ++ |
| E. coli | ECO 10 | ++ |
| E. coli | ECO 11 | ++ |
| E. coli | ECO 12 | ++ |
| Shigella boydii | NCTC 9327 | ++ |
| Shigella boydii | NCTC 9732 | ++ |
| Shigella boydii | NCTC 9850 | ++ |
| Shigella dysenteriae (type 4) | NCTC 9759 | ++ |
| Shigella dysenteriae (type 2) | NCTC 9952 | ++ |
| Shigella dysenteriae (type 3) | NCTC 9720 | ++ |
| Shigella flexneri | NCTC 8192 | ++ |
| Shigella flexneri | NCTC 9723 | ++ |
| Shigella flexneri | NCTC 9780 | ++ |
| Shigella sonnei | NCTC 9774 | ++ |
| Shigella sonnei | NCTC 8574 | ++ |
| Shigella sonnei | NCTC 10352 | ++ |
| Shigella sonnei | NCTC 8219 | ++ |
| Shigella sonnei | NCTC 8586 | ++ |
| Hafnia alvei | NCTC 8105 | ++ |
| Hafnia alvei | HAL 2 | ++ |
| K. pneumoniae | NCTC 10896 | ++ |
| K. pneumoniae | KPN 2 | ++ |
| K. pneumoniae | KPN 3 | ++ |
| K. pneumoniae | KPN 4 | ++ |
| K. oxytoca | KOX 1 | ++ |
| K. oxytoca | KOX 2 | ++ |
| C. freundii | NCTC 9750 | ++ |
| C. freundii | CFR 1 | ++ |
| C. freundii | CFR 2 | ++ |
| C. freundii | CFR 3 | ++ |
| C. freundii | CFR 4 | ++ |
| C. diversus | CDI 1 | ++ |
| C. diversus | CDI 2 | ++ |
| Serratia marcescens | NCTC 10211 | ++ |
| Serratia spp. | SEX 1 | ++ |
| Serratia spp. | SEX 2 | ++ |
| Serratia spp. | SEX 3 | ++ |
| Serratia spp. | SEX 4 | ++ |
| Aeromonas hydrophila | NCTC 8049 | ++ |
| Aeromonas caviae | NCTC 10852 | ++ |
| Aeromonas sobria | NCTC 11215 | ++ |
| E. cloacae | NCTC 11936 | ++ |
| E. cloacae | ECL 1 | ++ |
| E. cloacae | ECL 2 | ++ |
| E. cloacae | ECL 3 | ++ |
| E. cloacae | ECL 4 | ++ |
| E. aerogenes | NCIMB 10102 | ++ |
| E. aerogenes | EAE 1 | ++ |
| Salmonella typhimurium | NCTC 74 | ++ |
| Salmonella typhi | NCTC 8385 | ++ |
| Salmonella motevideo | SAX 55 | ++ |
| Salmonella oranienburg | SAX 56 | ++ |
| Salmonella hadar | SAX 57 | ++ |
| Salmonella panama | SAX 58 | ++ |
| Salmonella orthmarchen | SAX 59 | ++ |
| Salmonella alachia | SAX 60 | ++ |
| Y. enterocolitica | NCTC 11176 | − |
| Y. enterocolitica | NCTC 11177 | − |
| Y. enterocolitica | NCTC 11600 | − |
| Y. enterocolitica | NCTC 10460 | − |
| A. lwoffii | ATCC 15309 | − |
| A. baumanii | ATCC 19606 | − |
| A. calcoaceticus | ATCC 7844 | − |
| P. aeruginosa | NCTC 10662 | + |
| P. aeruginosa | ATCC 10145 | + |
| M. morganii | NCTC 235 | − |
| M. morganii | MMO 1 | + |
| M. morganii | MMO 2 | + |
| P. rettgeri | NCTC 7475 | + |
| Providencia stuartii | PST 1 | + |
| Providencia stuartii | PST 2 | + |
| Providencia alcalifaciens | PAL 1 | + |
| Providencia alcalifaciens | PAL 2 | − |
| P. mirabilis | NCTC 10975 | − |
| P. mirabilis | PMI 1 | − |
| P. mirabilis | PMI 2 | − |
| P. vulgaris | PVU 4 | − |
| P. vulgaris | PVU 2 | − |
| P. vulgaris | PVU 5 | − |
| P. penneri | PPE 1 | − |
| Vibrio parahaemolyticus | NCTC 12205 | − |
| Vibrio parahaemolyticus | NCTC 11344 | − |
| Vibrio fumissii | NCTC 11218 | − |
| Vibrio hollisae | NCTC 11640 | − |
| Vibrio cholera | NCTC 12945 | − |
| Vibrio cholera | NCTC 10732 | − |
| Vibrio cholera | NCTC 7270 | − |
| Vibrio cholera | NCTC 6585 | − |
| Vibrio cholera | NCTC 8021 | − |
| Vibrio parahaemolyticus | NCTC 10903 | − |
| Vibrio cincinnatiensis | NCTC 12012 | − |
| Vibrio parahaemolyticus | NCTC 10441 | − |
| Vibrio harveyi | NCTC 11346 | ++ |
| Vibrio vulnificus | NCTC 11067 | − |
| Vibrio metschnikovii | NCTC 8443 | ++ |
| Vibrio cholerae | NCTC 8042 | − |
| Vibrio cholerae | NCTC 10255 | − |
| Vibrio cholerae | NCTC 10954 | − |
| Vibrio mimicus | NCTC 11435 | − |
| Vibrio anguillarum | NCTC 12159 | − |
| Vibrio vulnificus | NCTC 11066 | − |
| Vibrio fluvialis | NCTC 11327 | ++ |
| Vibrio parahaemolyticus | NCTC 10884 | − |
| Vibrio cholerae | NCTC 7254 | − |
| Vibrio alcaligenes | NCTC 12160 | − |

Abbreviations:
NCTC National Collection of Type Cultures (UK)
ATCC American Type Culture Collection.
Key
+ Positive reaction with the substrate
++ Strong positive reaction with the substrate
− No detectable reaction

TABLE 2

Hydrolysis of 3'4'-dihydroxyflavone-β-ribofuranoside by Gram positive organisms

| Strain | Reference No. | β-Ribofuranoside |
|---|---|---|
| Streptococcus oralis | NCTC11427 | − |
| Streptococcus sanguis | NCTC 7863 | − |
| Streptococcus constellatus | NCTC 11325 | − |
| Streptococcus mitis | NCTC 12261 | − |
| Streptococcus salivarius | NCTC 8618 | − |
| Streptococcus crista | NCTC 12479 | − |
| Streptococcus vestibularis | NCTC 12166 | − |
| Streptococcus gordonii | NCTC 7865 | − |
| Streptococcus pneumoniae | NCTC 7465 | − |
| Streptococcus agalactiae | NCTC 8181 | − |
| Streptococcus milleri | wild | − |
| Haemolytic streptococcus A | 1 | − |
| Haemolytic streptococcus A | 2 | − |
| Haemolytic streptococcus A | 3 | − |
| Haemolytic streptococcus B | 1 | − |
| Haemolytic streptococcus B | 2 | − |
| Haemolytic streptococcus B | 3 | − |
| Haemolytic streptococcus C | 1 | − |
| Haemolytic streptococcus C | 67736 | − |
| Haemolytic streptococcus C | 68350 | − |
| Haemolytic streptococcus G | 1 | − |

TABLE 2-continued

Hydrolysis of 3'4'-dihydroxyflavone-β-ribofuranoside by Gram positive organisms

| Strain | Reference No. | β-Ribofuranoside |
|---|---|---|
| *Haemolytic streptococcus* G | 2 | − |
| *Haemolytic streptococcus* G | 3 | + |
| *Listeria seerigeri* | PHLS wild | − |
| *Listeria innocua* | PHLS wild | − |
| *Listeria ivanovii* | PHLS wild | + |
| *Arcanobacterium haemolyticus* | NCTC 52 | + |
| *Bacillus licusniforms* | NCIMB 9375 | − |
| *Bacillus cereus* | NCTC | − |
| *Corynebacterium diphtheria* | NEQAS | ++ |
| *C. diphtheriae* | NCTC 10356 | ++ |
| *C. diphtheriae* | NCTC 11397 | ++ |
| *C. diphtheriae* | NCTC 3987 | + |
| *Staphylococcus aureus* | 1 | ++ |
| *Staphylococcus aureus* | 2 | ++ |
| *Staphylococcus aureus* | 3 | ++ |
| *Staphylococcus aureus* | 4 | ++ |
| *Staphylococcus aureus* | 5 | ++ |
| *Staphylococcus haemolyticus* | RB 66 | + |
| *Staphylococcus haemolyticus* | RB 67 | + |
| *Staphylococcus haemolyticus* | RB 68 | + |
| *Staphylococcus haemolyticus* | RB 69 | + |
| *Staphylococcus haemolyticus* | RB 70 | + |
| *Staphylococcus epidermidis* | RB60 | ++ |
| *Staphylococcus epidermidis* | RB62 | + |
| *Staphylococcus epidermidis* | RB63 | + |
| *Staphylococcus epidermidis* | RB64 | + |
| *Staphylococcus epidermidis* | RB65 | + |
| *Staphylococcus saprophyticus* | 1 | ++ |
| *Staphylococcus saprophyticus* | 2 | ++ |
| *Staphylococcus saprophyticus* | 3 | ++ |
| *Staphylococcus saprophyticus* | 4 | ++ |
| *Staphylococcus saprophyticus* | 5 | ++ |
| *Enterococcus raffinosis* | NCTC 13192 | + |
| *Enterococcus mundtii* | NCTC 12363 | + |
| *Enterococcus durans* | NCTC 8307 | − |
| *Enterococcus gallinarum* | NCTC 11428 | + |
| *Enterococcus faecium* | 121285 - wild '99 | − |
| *Enterococcus casseflavus* | NCTC 12361 | − |
| *Enterococcus faecalis* | 1 | − |
| *Enterococcus faecalis* | 2 | + |
| *Enterococcus faecalis* | 3 | + |
| *Enterococcus faecalis* | 4 | + |
| *Enterococcus faecalis* | 5 | + |
| *Enterococcus faecalis* | 6 | + |
| *Enterococcus faecalis* | 7 | + |
| *Enterococcus faecium* | 1 | − |
| *Enterococcus faecium* | 2 | − |
| *Enterococcus faecium* | 3 | − |
| *Enterococcus faecium* | 4 | + |
| *Enterococcus faecium* | 5 | − |
| *Enterococcus faecium* | 6 | + |
| *Enterococcus faecium* | 7 | − |
| NEGATIVE CONTROL | | − |

Key
+ Positive reaction with the substrate
++ Strong positive reaction with the substrate
− No detectable reaction

EXAMPLE 3

Further substrates for the detection of β-D-ribofuranosidase activity were tested.

The same evaluation method as described above in Example 2 was utilised.

i) 3,4-dihydroxybenzaldehyde-4-β-ribofuranoside (produced in Example 1.4).

Dark brown colonies indicative of β-D-ribofuranosidase activity were visible for *S. sonnei* and *K. pneumoniae*. A weaker reaction and therefore paler colonies were seen for *E. coli* and *E. aerogenes*. A small zone of diffusion was visible around all positive colonies. The β-D-ribofuranosidase negative strains showed no signs of activity and formed cream colonies.

ii) 3',4'-dihydroxyaurone-4'-β-ribofuranoside (produced in Example 1.7).

As in previous tests, a selection of β-D-ribofuranosidase positive and negative strains were inoculated onto agar plates and incubated. Positive strains produced pale brown colonies indicating a weak reaction only.

iii) 3,4-dihydroxybenzaldehydedesemicarbazone-4-β-ribofuranoside (produced in Example 1.5).

As in previous tests, a selection of β-D-ribofuranosidase positive and negative strains were inoculated onto agar plates and incubated. After incubation all β-D-ribofuranosidase positive organisms grew as diffuse brown colonies and non-β-D-ribofuranosidase producing organisms grew as cream colonies.

The results of the tests are shown in Table 3 below

TABLE 3

Evaluation of chromogenic riboside substrates with respect to bacterial growth and colorial appearance

| | Colony colour (degree of colour diffusion from colony) | | |
|---|---|---|---|
| Organism | 3,4-dihydroxybenz-aldehyde-4-β-ribofuranoside | 3',4'-dihydroxy-aurone-4'-β-ribofuranoside | 3,4-dihydroxybenz-aldehydesemi-carbazone-4-β-ribofuranoside |
| *Escherichia coli* | pale brown (+) | brown (+++) | brown (++) |
| *Shigella sonnei* | brown (+) | brown (+++) | brown (++) |
| *Klebsiella pneumoniae* | brown (+) | ■ | brown (++) |
| *Enterobacter aerogenes* | pale brown (+) | ■ | brown (++) |
| *Yersinia enterocolitica* | cream | ■ | ■ |
| *Acinetobacter lwoffii* | cream | pale brown | ■ |
| *Salmonella* sp. | ■ | brown (+++) | brown (++) |
| *Proteus mirabilis* | ■ | pale brown | ■ |
| *Staphyococcus aureus* | ■ | pale brown | cream |

Key:
−    no diffusion
+    small zone
++    medium zone
+++    large zone
■    Not tested

EXAMPLE 4

Synthesis of 5-bromo-4-chloro-3-indolyl β-D-ribofuranoside (X-β-D-ribofuranoside)

The reaction was conducted in a 500 ml two-necked flask equipped with a magnetic stirrer.

To a mixture of 2,3,5-tri-O-acetyl-α/β-D-ribofuranosyl trichloroacetimide [I. Chiu-Machado et al., (1995), J. Carbohydrate. Chem. 14, 551 et seq.] (145.0 g) and 3 Å molecular sieves (2.0 g) in dry dichloromethane (300 ml) was added dry 1-acetyl-5-bromo-4-chloroindoxyl (X—OH) (82.9 g) and the whole mixture was stirred at room temperature for 10 mins. TMS-triflate (8 ml) was then added in one portion by syringe and the reaction was left stirring at room temperature for 1 hour. The mixture was then poured into dichloromethane (3 L) and washed with 1M sodium hydroxide (4×2 L). The organic layer was separated, filtered through celite and concentrated, in vacuo, to low volume (approx. 1 L). The organic layer was then further washed with 1M sodium hydroxide (6×1 L) and deionised water (1 L) After drying (magnesium sulfate) it was filtered through celite and concentrated, in vacuo, to afford the crude protected product as a dark brown solid (87.4 g).

The dark brown solid was examined by tlc and found to contain two main products with $R_f$ values of approximately 0.37 (the protected β-ribofuranoside) and 0.43. [Silica gel plates, 60/80 petroleum ether, ethyl acetate 1:1 v/v, uv at 254 nm]. Flash chromatography of the crude product on Silica Gel C60 (600 g) using 60/80 petroleum ether/ethyl acetate/ triethylamine 1:1:0.05 v/v/v as the eluting solvent gave the protected product as a brown oil (55 g). The oil was mainly a mixture of the X-β-D-ribofuranoside tetraacetate and the contaminant with $R_f$ 0.43. This oil was taken up in warm methanol (30 ml) and after leaving at ambient temperature a precipitate was formed. After 16 hours, the cream coloured solid consisting almost entirely of material with $R_f$ value 0.43 was removed by filtration, and the filtrate concentrated at 40° C. in vacuo to afford X-β-D-ribofuranoside tetraacetate as a brown oil (33.6 g).

X-β-D-ribofuranoside tetraacetate (30 g) was dissolved in methanol (200 ml) and 5 ml of a solution of sodium methoxide (made from 1 g sodium in 20 ml of methanol) was added dropwise until the solution reached pH 10. The solution was left standing at room temperature for 90 mins. then concentrated, in vacuo, to a brown tarry oil. The oil was triturated in acetone (500 ml). A grey solid precipitated and this was removed by vacuum filtration. The solid was discarded and the filtrate was concentrated in vacuo, to a brown oil (19.3 g). The oil was triturated with methanol (80 ml) and the product precipitated as a pale blue solid which was recovered by filtration (2.57 g). The filtrate was concentrated, in vacuo, and triturated with methanol (30 ml) to obtain a second crop as a pale cream solid that was also recovered by filtration (4.04 g). Both crops were combined and washed with cold acetone (approx. 20 ml) followed by filtration to recover the title compound as a white solid (approx. 2.5 g).

EXAMPLE 5

Comparison of the Attributes of Substrates For β-D-ribofuranosidase

The following media were produced to demonstrate the utility of the compounds of the current invention.

| Medium A (components per liter) | |
|---|---|
| Columbia agar (Oxoid) | 40 g |
| 5-Bromo-4-chloro-3-indolyl β-D-ribofuranoside 6-chloro-3-indolyl β-D-glucopyranoside | 200 mg |
| Medium B (components per liter) | |
| Columbia agar (Oxoid) | 40 g |
| 3'4'-dihydroxyflavone-4'-β-D-ribofuranoside | 300 mg |
| 6-chloro-3-indolyl β-D-glucopyranoside | 200 mg |
| Ferric ammonium citrate | 500 mg |
| Medium C (components per liter) | |
| Columbia agar (Oxoid) | 40 g |
| 5-Bromo-4-chloro-3-indolyl β-D-ribofuranoside | 80 mg |
| 3,4-cyclohexenoesculetin-β-D-galactopyranoside | 300 mg |
| Isopropyl-β-D-thiogalactopyranoside | 30 mg |
| Ferric ammonium citrate | 500 mg |
| Medium D (components per liter) | |
| Columbia agar (Oxoid) | 40 g |
| 5-Bromo-4-chloro-3-indolyl β-D-ribofuranoside | 80 mg |
| 3'4'-dihydroxy-3-methoxyflavone-4'-β-D-galactopyranoside | 300 mg |
| Isopropyl-β-D-thiogalactopyranoside | 30 mg |
| Ferric ammonium citrate | 500 mg |
| Medium E (components per liter) | |
| Columbia agar (Oxoid) | 40 g |
| 5-Bromo-4-chloro-3-indolyl β-D-ribofuranoside | 80 mg |
| Medium F (components per liter) | |
| Columbia agar (Oxoid) | 40 g |
| 3'4'-dihydroxyflavone-4'-β-D-ribofuranoside | 300 mg |
| Ferric ammonium citrate | 500 mg |

All components were added to 1 liter of deionised water and autoclaved at 116° C. for 10 minutes. Culture plates were prepared from molten agar at 50° C. and dried. Various control strains with known enzymatic characteristics were prepared at a suspension of approximately $10^8$ cfu/ml using a densitometer. 10 µl of this suspension was inoculated onto each of the different types of media and incubated overnight at 37° C. The cultural appearance of the various strains tested are shown in Table 4.

TABLE 4

Table 4: Colonial appearance of various strains on various chromogenic agars.

| | A | B | C | D | E | F |
|---|---|---|---|---|---|---|
| *Enterobacter cloacae* NCTC 11936 | Purple | Black | Black | Black | Green | Black |
| *Escherichia coli* NCTC 10418 | Green | Black | Black | Black | Green | Black |
| *Klebsiella pneumoniae* NCTC 10896 | Purple | Black | Black | Black | Green | Black |
| *Salmonella typhimurium* NCTC 74 | Green | Black | Green | Green | Green | Black |
| *Serratia marcescens* NCTC 10211 | Purple | Black | Green | Black | Green | Black |
| *Yersinia enterocolitica* NCTC 11176 | Colourless | Colourless | Colourless | Grey/black | Colourless | Colourless |

| | E |
|---|---|
| *Acinetobacter lwoffii* ATCC 15309 | Colourless |
| *Aeromonas hydrophila* NCTC 8049 | Green |
| *Citrobacter freundii* NCTC 9750 | Green |
| *Enterobacter aerogenes* NCIMB 10102 | Green |
| *Escherichia coli* 0157 NCTC 12079 | Green |
| *Shigella boydii* NCTC 9327 | Green |
| *Vibrio cholerae* NCTC 12945 | Colourless |
| *Pseudomonas aeruginosa* NCTC 10662 | Colourless |

EXAMPLE 6

3'4'-dihydroxy-3-methoxy-flavone-4'-β-D-ribofuranoside

The substrate shown in the heading was synthesised from 3',4'-Dihydroxy-3-methoxyflavone (F. A. A. van Acker et al., *J. Med. Chem.*, 43, 3752-3760, (2000)) by a method analogous to example 1.

The substrate was evaluated using the general method of example 2 but using a range of different metal salts and a culture of *E. coli* alone. The metal salts shown in Table 5, below, were used at a concentration of 500 mg/l.

TABLE 5

Evaluation of 3',4'-dihydroxy-3-methoxy-flavone-4'-β-D-ribofuranoside with metal salts forming chelates

| Metal | Colour of colonies |
|---|---|
| Zn | No growth |
| Co | No growth |
| Mn | Pale orange |
| Sn | Yellow |
| Ba | Yellow |
| Al | Yellow |
| Sr | Yellow |
| Bi | Rusty orange |
| Fe | Brown |
| No metal | Diffuse yellow |

When the aluminium salt-containing medium was used with a mixed culture of *E. coli* and *Yersinia enterocolitica*, the *E. coli* colonies were bright yellow and stood out very clearly. There was substantially no diffusion into the *Y. enterocolitica* colonies (negative for this substrate, thus colourless) even when the colonies were almost coincident.

The invention claimed is:

1. A method of detecting β-D-ribofuranosidase activity on a solid medium including the steps:
   a) contacting a chromogenic β-D-ribofuranoside comprising a β-D-ribofuranosyl group and a chromogenic portion, with a sample comprising bacteria suspected of containing β-D-ribofuranosidase activity, on a solid growth medium;
   b) incubating the mixture on the growth medium under conditions such that bacterial growth occurs; and
   c) determining whether an indicator is formed in the solid medium, and
   d) correlating whether an indicator is formed in step c) with β-D-ribofuranosidase activity,
   wherein the chromogenic portion cleaved by β-D-ribofuranosidase from the β-D-ribofuranosyl group to release a chromogenic product and form the indicator which is or is formed from the chromogenic product and is substantially non-diffusible in the solid medium.

2. The method of claim 1 wherein the bacteria are is selected from the group consisting of the genus *Yersinia*, the genus *Shigella*, the genus *Vibrio*, *Corynebacterium diphtheriae* and *Arcanobacterium haemolyticum*.

3. The method of claim 1 which also includes the step of contacting the chromogenic product with a developer to form said indicator.

4. The method of claim 3 when the chromogenic β-D-ribofuranoside is represented by one of the formulae I and II

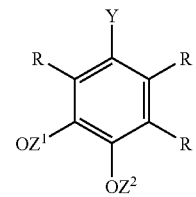

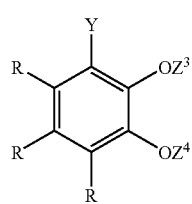

where Y and R are hydrogen or organic groups which do not interfere with enzyme cleavage or formation of the indicator and each of $Z^1$, $Z^2$, $Z^3$ and $Z^4$ can be H or a β-D-ribofuranosyl moiety, provided $Z^1$ and $Z^2$ or $Z^3$ and $Z^4$ are not simultaneously H and the developer is a metal ion.

5. The method of claim 1 further comprising contacting the chromogenic product with a developer to form said indicator, wherein said developer is present in the solid medium.

6. The method of claim 1 wherein the substantially non-diffusible indicator is visible using visible incident light.

7. The method of claim 1 wherein the chromogenic portion is an a derivative of a hydroxyl compound selected from the group consisting of 1,2-dihydroxy benzene derivatives, indoxyls and p-naphthol-benzein.

8. The method of claim 7 in which the chromogenic β-D-ribofuranoside is selected from the group consisting of catechol-β-D-ribofuranoside, 3',4'-dihydroxyflavone-4'-β-D-ribofuranoside, quercetin-4'-β-D-ribofuranoside, 3,4-dihydroxybenzaldehyde-4-β-D-ribofuranoside, 3,4-dihydroxychalcone-4-β-D-ribofuranoside, 4-nitrocatechol-1-β-D-ribofuranoside, 3,3',4'-trihydroxyflavone-4'-β-D-ribofuranoside, 3',4'-dihydroxy-3-$C_{1-6}$-alkoxyflavone-4'-β-D-ribofuranoside and 3',4'-dihydroxyaurone-4'-β-D-ribofuranoside, 3-methoxy-3',4'-dihydroxyflavone-4'-β-D-ribofuranoside and 5-bromo-4-chloro-3-indolyl-β-D-ribofuranoside.

9. The method of claim 7 wherein the chromogenic portion is an O-β-D-ribofuranosyl 1,2-dihydroxybenzene derivative.

10. The method of claim 9 wherein the chromogenic portion comprises a dihydroxybenzaldehyde, dihydroxybenzophenone, dihydroxyflavonoid, dihydroxyaurone or dihydroxychalcone.

11. The method of claim 9 in which the chromogenic β-D-ribofuranoside is represented by one of the formulae I and II

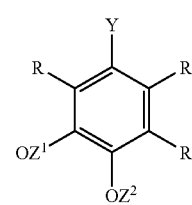

-continued

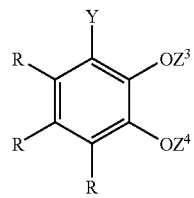

where Y and R are hydrogen or organic groups which do not interfere with beta-D-ribofuranosidase cleavage or formation of the indicator and each of $Z^1$, $Z^2$, $Z^3$ and $Z^4$ can be H or a β-D-ribofuranosyl moiety, provided $Z^1$ and $Z^2$ or $Z^3$ and $Z^4$ are not simultaneously H.

12. The method of claim 11 wherein Y and R are organic moieties containing less than 20 atoms.

13. The method of claim 11 wherein each R is selected from the group consisting of H, $C_1$ to $C_6$-alkyl, -alkoxy and -hydroxyalkyl, halogeno, nitro, acyl, aryl and amido groups, or two adjacent groups R may be joined to form a fused ring system with the ring shown in formulae I and II, such a fused ring optionally having an aromatic character, and optionally including one or more heteroatoms.

14. The method of claim 13 wherein each R is selected from the group consisting of H, $C_1$ to $C_6$-alkyl, -alkoxy and -hydroxyalkyl, halogeno, nitro, acyl, aryl and amido groups, which R groups are not linked to one another.

15. The method of claim 14 wherein Y comprises a substituted or unsubstituted aryl or heteroaryl group containing 5 to 18 ring atoms.

16. The method of claim 15 wherein Y has the structure of IX or X

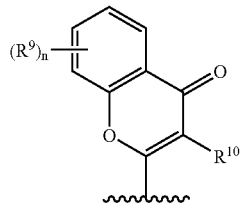

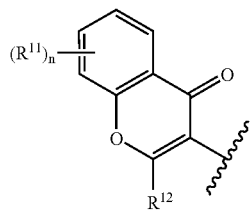

wherein $R^9_n$ and $R^{11}_n$ are independently selected from the group consisting of hydroxyl, $C_{1-24}$-alkyl, $C_{2-24}$-alkenyl, $C_{1-6}$-alkoxy, acyl halogen, nitro, aryl and acyloxy groups and $R^{10}$ and $R^{12}$ are selected from the group consisting of hydrogen, hydroxyl, $C_{1-24}$-alkyl, $C_{2-24}$-alkenyl, $C_{1-6}$-alkoxy, acyl halogen, nitro, aryl and acyloxy groups, all of which do not interfere with enzyme action or metal ion chelation, and n is 0, 1 or 2.

17. A method of detecting β-D-ribofuranosidase activity on a solid medium including the steps:
a) contacting on a solid medium a chromogenic β-D-ribofuranoside, comprising a β-D-ribofuranosyl group and a chromogenic portion said chromogenic portion being cleavable by β-D-ribofuranosidase from the β-D-ribofuranosyl group releasing a chromogenic product, with a substance suspected of containing β-D-ribofuranosidase activity
b) contacting said chromogenic product with a developer to form an indicator which is substantially non-diffusible in the solid medium, and
c) detecting whether β-D-ribofuranosidase activity is present by determining whether said indicator is formed.

18. The method of claim 17 wherein the substantially non-diffusible indicator is visible using visible incident light.

19. The method of claim 17 wherein the chromogenic portion is an O-linked ribofuranosyl derivative of a hydroxyl compound selected from the group consisting of 1,2-dihydroxy benzene derivatives, indoxyls and p-naphthol-benzein and derivatives thereof.

20. The method of claim 19 in which the chromogenic β-D-ribofuranoside is represented by one of the formulae I and II

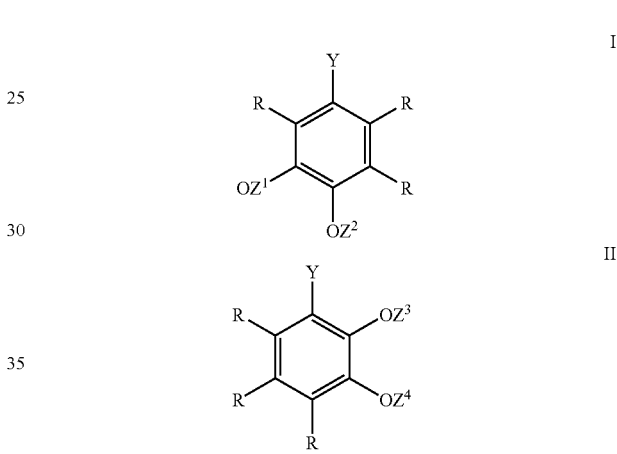

where Y and R are hydrogen or organic groups which do not interfere with beta-D-ribofuranosidase cleavage or formation of the indicator and each of $Z^1$, $Z^2$, $Z^3$ and $Z^4$ can be H or a β-D-ribofuranosyl moiety, provided $Z^1$ and $Z^2$ or $Z^3$ and $Z^4$ are not simultaneously H.

21. The method of claim 20 wherein each R is selected from the group consisting of H, $C_1$ to $C_6$-alkyl, -alkoxy and -hydroxyalkyl, halogeno, nitro, acyl, aryl and amido groups, or two adjacent groups R may be joined to form a fused ring system with the ring shown in formulae I and II, such a fused ring optionally having an aromatic character, and optionally including one or more heteroatoms, and
Y comprises a substituted or unsubstituted aryl or heteroaryl group containing 5 to 18 ring atoms.

22. The method of claim 21 wherein Y has the structure of IX or X

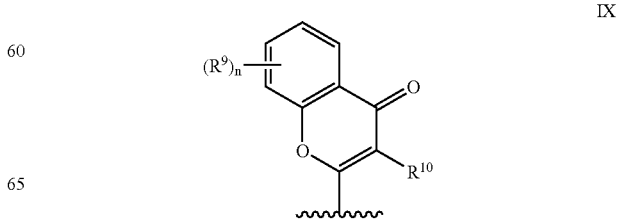

-continued

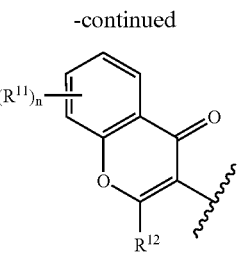

X wherein $R^9_n$ and $R^{11}_n$ are independently selected from the group consisting of hydroxyl, $C_{1-24}$-alkyl, $C_{2-24}$-alkenyl, $C_{1-6}$-alkoxy, acyl halogen, nitro, aryl and acyloxy groups and $R^{10}$ and $R^{12}$ are selected from the group consisting of hydrogen, hydroxyl, $C_{1-24}$-alkyl, $C_{2-24}$-alkenyl, $C_{1-6}$-alkoxy, acyl halogen, nitro, aryl and acyloxy groups, all of which do not interfere with enzyme action or metal ion chelation, and n is 0, 1 or 2.

23. A method of detecting β-D-ribofuranosidase activity on a solid agar medium including the steps as a preliminary step, growing microbes on a solid agar medium, wherein a chromogenic β-D-ribofuranoside is present on the solid agar medium during the preliminary growing step;

a) contacting on the agar medium the chromogenic β-D-ribofuranoside, comprising a β-D-ribofuranosyl group and a chromogenic portion said chromogenic portion being cleavable by β-D-ribofuranosidase from the β-D-ribofuranosyl group releasing a chromogenic product and forming an indicator which is or is formed from the chromogenic product and is substantially non-diffusible in the agar medium, with a substance suspected of containing β-D-ribofuranosidase activity; wherein the substance suspected of containing β-D-ribofuranosidase activity comprises a substance of microbial origin;

b) detecting whether β-D-ribofuranosidase activity is present by determining whether said indicator is formed.

24. The method of claim 23 further comprising contacting the chromogenic product with a developer to form said indicator.

25. The method of claim 24, wherein said developer is present in the solid agar medium in the preliminary growing step.

26. A method of detecting β-D-ribofuranosidase activity on a solid medium including the steps of a) contacting on a solid medium a substance suspected of containing β-D-ribofuranosidase activity with a chromogenic β-D-ribofurano substance having one of the formulae I and II

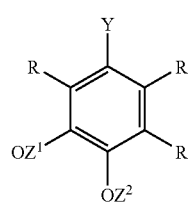

I

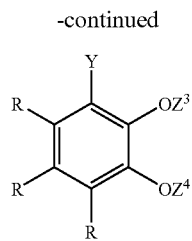

II where Y comprises an aryl or heteroaryl group containing 5 to 18 ring atoms, each R is selected from the group consisting of H, $C_1$ to $C_6$-alkyl, -alkoxy and -hydroxyalkyl, halogen, nitro, acyl, aryl and amido groups, or two adjacent groups R may be joined to form a fused ring system with the ring shown in formulae I and II, such a fused ring optionally having an aromatic character, and optionally including one or more heteroatoms, each of $Z^1$, $Z^2$, $Z^3$ and $Z^4$ can be H or a β-D-ribofuranosyl moiety, provided $Z^1$ and $Z^2$ or $Z^3$ and $Z^4$ are not simultaneously H b) detecting whether β-D-ribofuranosidase activity is present by determining whether chromogenic product has been formed.

27. The method of claim 26 wherein Y has the structure of IX or X

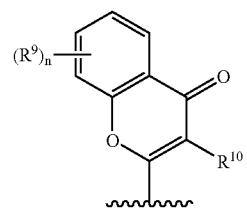

IX

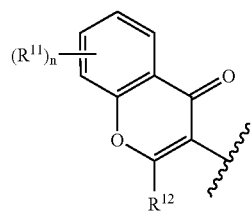

X wherein $R^9_n$ and $R^{11}_n$ are independently selected from the group consisting of hydroxyl, $C_{1-24}$-alkyl, $C_{2-24}$-alkenyl, $C_{1-6}$-alkoxy, acyl halogen, nitro, aryl and acyloxy groups and $R^{10}$ and $R^{12}$ are selected from the group consisting of hydrogen, hydroxyl, $C_{1-24}$-alkyl, $C_{2-24}$-alkenyl, $C_{1-6}$-alkoxy, acyl halogen, nitro, aryl and acyloxy groups, all of which do not interfere with beta-D-ribofuranosidase activity or metal ion chelation, and n is 0, 1 or 2.

* * * * *